United States Patent
Pruitt et al.

(10) Patent No.: US 10,913,224 B2
(45) Date of Patent: Feb. 9, 2021

(54) OPHTHALMIC DEVICES FOR DELIVERY OF HYDROPHOBIC COMFORT AGENTS

(71) Applicant: Novartis AG, Basel (CH)

(72) Inventors: John Dallas Pruitt, Suwanee, GA (US); Lynn Cook Winterton, Keller, TX (US); Jared Nelson, Buford, GA (US)

(73) Assignee: Alcon Inc., Fribourg (CH)

( * ) Notice: Subject to any disclaimer, the term of this patent is extended or adjusted under 35 U.S.C. 154(b) by 169 days.

(21) Appl. No.: 16/181,763

(22) Filed: Nov. 6, 2018

(65) Prior Publication Data

US 2019/0070804 A1 Mar. 7, 2019

Related U.S. Application Data

(62) Division of application No. 12/629,913, filed on Dec. 3, 2009, now Pat. No. 10,155,349.

(60) Provisional application No. 61/120,155, filed on Dec. 5, 2008.

(51) Int. Cl.
*A61K 9/00* (2006.01)
*G02B 1/04* (2006.01)
*B29D 11/00* (2006.01)

(52) U.S. Cl.
CPC ...... *B29D 11/00067* (2013.01); *A61K 9/0051* (2013.01); *G02B 1/043* (2013.01)

(58) Field of Classification Search
None
See application file for complete search history.

(56) References Cited

U.S. PATENT DOCUMENTS

2006/0177483 A1 8/2006 Byrne et al.
2007/0296914 A1 12/2007 Hong et al.

FOREIGN PATENT DOCUMENTS

EP 2461767 B1 5/2013
KR 100727008 B1 6/2007
WO 2009/085902 A1 7/2009

OTHER PUBLICATIONS

Statement on a Nonproprietary Name Adopted by the USAN Council: Stenfilcon A, Apr. 24, 2013.
U.S. Appl. No. 61/008,554, filed Dec. 20, 2007,Certified Copy of Priority Document.
Kenneth A. Connors, Chemical Kinetics: The Study of Reaction Rates in Solution, 1990, VCH Publishers, Inc., Chapter 2-Simple Rate Equations, pp. 17-19.
Surafel Mulugeta et al., Identification and absolute configuration of dihydroxy-arachiodonic acids formed by oxygenation of 5S-HETE by native and aspirin-acetylated COX-2, Journal of Lipid Research, vol. 51, 2010, pp. 575-585.
Vasiliki Papadopoulou et al., On the use of the Weibull function for the discernment of drug release mechanisms, International Journal of Pharmaceutics, 309, 2006, pp. 44-50.
William G. Pitt et al., Loading and Release of a Phospholipid From Contact Lenses, Optometry and Vision Science, vol. 88, No. 4, 2011, American Academy of Optometry, pp. 502-506.
Preeti Subramanian et al., A Novel Inhibitor of 5-Lipoxygenase (5-LOX) Prevents Oxidative Stress-Induced Cell Death of Retinal Pigment Epithelium (RPE) Cells, Investigative Ophthalmology & Visual Science, 57(11), 2016, pp. 1-18.

*Primary Examiner* — Gigi G Huang
(74) *Attorney, Agent, or Firm* — Jian Zhou

(57) ABSTRACT

The invention relates to a soft hydrogel contact lens, especially a silicone hydrogel contact lens, which has a capability of delivering a hydrophobic comfort agent into the eye of a wearer. The hydrophobic comfort agent includes without limitation a monoglyceride, a diglyceride, a triglyceride, a glycolipid, a glyceroglycolipid, a sphingolipid, a sphingoglycolipid, a phospholipid, a fatty acid, a fatty alcohol, a hydrocarbon having a $C_{12}$-$C_{28}$ chain in length, a mineral oil, a silicone oil, or a mixture thereof. It can be released from the soft hydrogel contact lens into the eye of a wearer when being worn so as to strengthen and stabilize the tear film lipid layer and alleviate the dryness of the eye.

4 Claims, No Drawings

OPHTHALMIC DEVICES FOR DELIVERY OF HYDROPHOBIC COMFORT AGENTS

This application is a divisional application of U.S. patent application Ser. No. 12/629,913 filed 3 Dec. 2009, which claims the benefit under 35 USC § 119 (e) of U.S. provisional application No. 61/120,155 filed on Dec. 5, 2008, herein incorporated by reference in its entirety.

The present invention relates to ophthalmic devices, in particular contact lenses, which are capable of gradually releasing one or more hydrophobic comfort agents during wear. The present invention also provides methods for making ophthalmic devices of the invention.

BACKGROUND OF THE INVENTION

The tear film normally includes a three layer structure: a lipid layer, a middle aqueous layer, and a mucinous layer. The lipid layer is the outermost layer and derived from the secretions of the Meibomian glands. It is likely composed of 2 phases: a thin polar phase adjacent to the aqueous-mucin phase and a thick nonpolar phase associated with both the polar phase and the air interface (McCully and Shine, Tr. Am. Soc. Vol. XCV, 1997). The middle aqueous layer is provided by the major and minor lacrimal glands, and contains water-soluble substances. The innermost mucinous layer is composed of glycoprotein, mucin, and overlies the corneal and conjunctival epithelial cells. The epithelial cell membranes are composed of lipoproteins and thus generally hydrophobic. When any of the tear film components is deficient, the tear film will break up, and dry spots will form on the corneal and the conjunctival epithelium. Deficiency of any of the three components (aqueous, mucin or lipid layers) may result in dryness of the eye.

In recent years, a great of efforts have been made to develop contact lenses capable of delivering comfort agents. For example, U.S. Pat. Nos. 4,045,547, 4,042,552, 5,198,477, 5,219,965, 6,367,929 and 6,822,016, 7,279,507 and commonly owned co-pending U.S. patent application publication Nos. 2006/0079598A1 and 2006/0251696A1 (herein incorporated by reference in their entireties) disclose that leachable wetting agents can be incorporated into a lens formulation for making the contact lenses, to improve the surface hydrophilicity and/or wearing comfort of contact lenses.

Another example is to incorporate into contact lenses one or more bioactive agents the release of which is triggered by one or more tear components produced by the eye when the devices comes into contact with the tears, as disclosed in a commonly owned co-pending U.S. patent application publication No. 2008/0124376A1 (herein incorporated by reference in its entirety).

However, there are no contact lenses capable of delivering hydrophobic comfort agents which are the constituents or the likes of the tear film lipid layer and can strengthen and stabilize the tear film lipid layer and alleviate the dryness of the eye. Therefore, there exists a need for contact lenses capable of delivering hydrophobic comfort agents in a sustainable manner over an extended period of time.

SUMMARY OF THE INVENTION

The present invention, in one aspect, provides a soft hydrogel contact lens comprising a polymeric matrix and a hydrophobic comfort agent which is not covalently linked to the polymer matrix but distributed therein, wherein the polymeric matrix comprises hydrophobic units derived from a silicone-containing monomer or macromer and/or a hydrophobic monomer and hydrophilic units derived from a hydrophilic monomer or macromer, wherein the soft contact lens is characterized by its capability of gradually releasing the hydrophobic comfort agent from the polymer matrix into the eye of a wearer when being worn.

The present invention, in another aspect, provides an ophthalmic product comprising a sealed package which include a packaging solution and a soft hydrogel contact lens, wherein the hydrogel contact lens comprises a polymer matrix and a hydrophobic comfort agent which is not covalently linked to the polymer matrix but distributed therein, wherein the polymeric matrix comprises hydrophobic units derived from a silicone-containing monomer or macromer and/or a hydrophobic monomer and hydrophilic units derived from a hydrophilic monomer or macromer, wherein the soft contact lens is characterized by its capability of gradually releasing the hydrophobic comfort agent from the polymer matrix into the eye of a wearer when being worn.

The present invention, in a further aspect, provides a process for making a soft contact lens capable of gradually delivering a hydrophobic comfort agent during wearing of the contact lens. The method of the invention comprises the steps of: a) dipping a soft hydrogel contact lens in a solution containing a hydrophobic comfort agent and an organic solvent miscible with water, wherein the soft hydrogel contact lens comprises a polymer matrix including hydrophobic units derived from a silicone-containing monomer or macromer and/or a hydrophobic monomer and hydrophilic units derived from a hydrophilic monomer or macromer, wherein the organic solvent swells the soft hydrogel contact so as to allow the hydrophobic comfort agent to be incorporate into the polymer matrix of the soft hydrogel contact lens; b) hydrating the soft hydrogel contact lens comprising the comfort agent distributed therein in water or a buffered aqueous solution; and c) placing and sealing the hydrated soft hydrogel contact lens in a lens package containing a lens packaging solution.

The present invention, in still a further aspect, provides a method for making a soft contact lens capable of gradually delivering a hydrophobic comfort agent during wearing of the contact lens. The method of the invention comprises the steps of: a) obtaining a fluid prepolymer composition comprising a first organic solvent, an actinically-crosslinkable lens-forming material, and a hydrophobic comfort agent, wherein the actinically-crosslinkable lens-forming material comprises actinincally-crosslinkable groups and can be polymerized thermally or actinically to form the polymer matrix of the soft contact lens, wherein the actinically-crosslinkable lens-forming material comprises monomer, macromer, and/or prepolymer, wherein the hydrophobic comfort agent is free of any actinically-crosslinkable group; b) introducing an amount of the fluid prepolymer composition in a mold for making a contact lens; c) polymerizing the actinically-crosslinkable prepolymer in the mold to form the soft contact lens with the hydrophobic comfort agent being not covalently linked to the polymer matrix but being distributed therein in a substantially uniform manner; d) hydrating the resultant soft contact lens in water or an aqueous solution to replace the first organic solvent with water or the aqueous solution; e) packaging the hydrated soft contact lens in a container containing a packaging solution; and f) sterilizing the soft contact lens in the package, wherein the sterilized soft contact lens is capable of gradually releasing the hydrophobic comfort agent during wear, provided that the method is free of any extraction step with a second organic solvent.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a polymeric material which can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

"Hydrophilic," as used herein, describes a material or portion thereof that will more readily associate with water than with lipids.

A "monomer" means a low molecular weight compound that can be polymerized actinically. Low molecular weight typically means average molecular weights less than 700 Daltons. In accordance with the invention, a monomer can be a vinylic monomer or a compound comprising two thiol groups. A compound with two thiol groups can participate in thiol-ene step-growth radical polymerization with a monomer with vinyl group to form a polymer. Step-growth radical polymerization can be used in making contact lenses, as described in a commonly-owned copending U.S. patent application Ser. No. 12/001562, herein incorporated in reference in its entirety.

A "silicone-containing monomer" refers to a monomer which contains silicone and can be crosslinked actinically to obtain a polymer.

A "vinylic monomer", as used herein, refers to a monomer that has an ethylenically unsaturated group and can be polymerized actinically or thermally.

The term "olefinically unsaturated group" or "ethylenically unsaturated group" is employed herein in a broad sense and is intended to encompass any groups containing a >C=C< group. Exemplary ethylenically unsaturated groups include without limitation acryloyl, methacryloyl, allyl, vinyl, styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

The term "fluid" as used herein indicates that a material is capable of flowing like a liquid.

A "hydrophilic monomer" refers to a monomer which can be polymerized actinically to form a polymer that is water-soluble or can absorb at least 10 percent by weight of water.

A "hydrophobic monomer" refers to a monomer which is polymerized actinically to form a polymer that is insoluble in water and can absorb less than 10 percent by weight water.

A "macromer" refers to a medium and high molecular weight compound which can be polymerized and/or crosslinked actinically. Medium and high molecular weight typically means average molecular weights greater than 700 Daltons. In accordance with the invention, a macromer can be a macromer with one or more ethylenically unsaturated groups or with two or more thiol groups, which can participate in either free radical chain growth polymerization or thiol-ene step-growth radical polymerization. Preferably, a macromer contains ethylenically unsaturated groups and can be polymerized actinically or thermally. A "siloxane-containing macromer" is a macromer which contains silicone and can be crosslinked actinically.

A "prepolymer" refers to a starting polymer which contains multiple actinically crosslinkable groups and can be cured (e.g., crosslinked) actinically to obtain a crosslinked polymer having a molecular weight much higher than the starting polymer.

"Actinically crosslinkable groups" refers to ethylenically unsaturated groups or thiol groups.

A "silicone-containing prepolymer" refers to a prepolymer which contains silicone and can be crosslinked actinically to obtain a crosslinked polymer having a molecular weight much higher than the starting polymer.

"Molecular weight" of a polymeric material (including monomeric or macromeric materials), as used herein, refers to the number-average molecular weight unless otherwise specifically noted or unless testing conditions indicate otherwise.

"Polymer" means a material formed by polymerizing one or more monomers.

As used herein, the term "multiple" refers to at least two, preferably at least three.

A "photoinitiator" refers to a chemical that initiates radical crosslinking/polymerizing reaction by the use of light. Suitable photoinitiators include, without limitation, benzoin methyl ether, diethoxyacetophenone, a benzoyl phosphine oxide, 1-hydroxycyclohexyl phenyl ketone, Darocur® types, and Irgacur® types, preferably Darocur® 1173, and Irgacur® 2959.

A "thermal initiator" refers to a chemical that initiates radical crosslinking/polymerizing reaction by the use of heat energy. Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is 2,2'-azobis(isobutyronitrile) (AIBN).

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. For example, a spatial limitation of UV radiation can be achieved by using a mask or screen that has a transparent or open region (unmasked region) surrounded by a UV impermeable region (masked region), as schematically illustrated in FIGS. 1-9 of U.S. Pat. No. 6,627,124 (herein incorporated by reference in its entirety). The unmasked region has a well defined peripheral boundary with the unmasked region. The energy used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting a lens.

"Dye" means a substance that is soluble in a solvent and that is used to impart color. Dyes are typically translucent and absorb but do not scatter light. Any suitable biocompatible dye can be used in the present invention.

A "Pigment" means a powdered substance that is suspended in a liquid in which it is insoluble. A pigment can be a fluorescent pigment, phosphorescent pigment, pearlescent pigment, or conventional pigment. While any suitable pigment may be employed, it is presently preferred that the pigment be heat resistant, non-toxic and insoluble in aqueous solutions.

"Surface modification", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, plasma processes in which an ionized gas is applied to the surface of an article (see, for example, U.S. Pat. Nos. 4,312,575 and 4,632,844 herein incorporated by reference in its entirety); a surface treatment by energy other than plasma (e.g., a static electrical charge, irradiation, or other energy source); chemical treatments; the grafting of hydrophilic monomers or macromers onto the surface of an article; mold-transfer coating process disclosed in U.S. Pat. No. 6,719,929 (herein incorporated by reference in its entirety); the incorporation of wetting agents into a lens formulation for making contact lenses (i.e., surface treatment prior to polymerization) proposed in U.S. Pat. Nos. 4,045,547, 4,042,552, 5,198,477, 5,219,965, 6,367,929 and 6,822,016, 7,279,507 (herein incorporated by references in their entireties); reinforced mold-transfer coating disclosed in PCT Patent Application Publication No. WO2007/146137 (herein incorporated by reference in its entirety); and layer-by-layer coating ("LbL coating") obtained according to methods described in U.S. Pat. Nos. 6,451,871, 6,719,929, 6,793,973, 6,811,805, 6,896,926 (herein incorporated by references in their entireties).

Exemplary plasma gases and processing conditions are described in U.S. Pat. Nos. 4,312,575 and 4,632,844. The plasma gas is preferably a mixture of lower alkanes and nitrogen, oxygen or an inert gas.

"LbL coating", as used herein, refers to a coating that is not covalently attached to a contact lens or a mold half and is obtained through a layer-by-layer ("LbL") deposition of polyionic (or charged) and/or non-charged materials on the lens or mold half. An LbL coating can be composed of one or more layers.

As used herein, a "polyionic material" refers to a polymeric material that has a plurality of charged groups or ionizable groups, such as polyelectrolytes, p- and n-type doped conducting polymers. Polyionic materials include both polycationic (having positive charges) and polyanionic (having negative charges) materials.

Formation of an LbL coating on a contact lens or mold half may be accomplished in a number of ways, for example, as described in U.S. Pat. Nos. 6,451,871, 6,719,929, 6,793, 973, 6,811,805, 6,896,926 (herein incorporated by references in their entirety).

"Post-curing surface treatment", in reference to a silicone hydrogel material or a soft contact lens, means a surface treatment process that is performed after the formation (curing) of the hydrogel material or the soft contact lens in a mold.

A "hydrophilic surface" in reference to a silicone hydrogel material or a contact lens means that the silicone hydrogel material or the contact lens has a surface hydrophilicity characterized by having an averaged water contact angle of about 90 degrees or less, preferably about 80 degrees or less, more preferably about 70 degrees or less, more preferably about 60 degrees or less.

An "average contact angle" refers to a water contact angle (advancing angle measured by sessile drop method), which is obtained by averaging measurements of at least 3 individual contact lenses.

An "antimicrobial agent", as used herein, refers to a chemical that is capable of decreasing or eliminating or inhibiting the growth of microorganisms such as that term is known in the art.

"Antimicrobial metals" are metals whose ions have an antimicrobial effect and which are biocompatible. Preferred antimicrobial metals include Ag, Au, Pt, Pd, Ir, Sn, Cu, Sb, Bi and Zn, with Ag being most preferred.

"Antimicrobial metal-containing nanoparticles" refer to particles having a size of less than 1 micrometer and containing at least one antimicrobial metal present in one or more of its oxidation states.

"Antimicrobial metal nanoparticles" refer to particles which are made essentially of an antimicrobial metal and have a size of less than 1 micrometer. The antimicrobial metal in the antimicrobial metal nanoparticles can be present in one or more of its oxidation states. For example, silver-containing nanoparticles can contain silver in one or more of its oxidation states, such as $Ag^0$, $Ag^{1+}$, and $Ag^{2+}$.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

$$[(cm^3 \text{ oxygen})/(cm^2)(sec)(mm \text{ Hg})] \times 10^{-9}$$

The intrinsic "oxygen permeability", Dk, of a lens material does not depend on lens thickness. Intrinsic oxygen permeability is the rate at which oxygen will pass through a material. Oxygen permeability is conventionally expressed in units of barrers, where "barrer" is defined as:

$$[(cm^3 \text{ oxygen})(mm)/(cm^2)(sec)(mm \text{ Hg})] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm (oxygen transmissibility barrers/mm). In accordance with the invention, a high oxygen permeability in reference to a material or a contact lens characterized by apparent oxygen permeability of at least 40 barrers or larger measured with a sample (film or lens) of 100 microns in thickness.

The "ion permeability" through a lens correlates with the Ionoflux Diffusion Coefficient, D, which is determined by applying Fick's law as follows:

$$D=-n'/(A \times dc/dx)$$

In which: n'=rate of ion transport [mol/min]; A=area of lens exposed [mm$^2$]; D=Ionoflux Diffusion Coefficient [mm$^2$/min]; dc=concentration difference [mol/L]; dx=thickness of lens [mm]. An Ionoflux Diffusion Coefficient, D, of greater than about $1.5 \times 10^{-6}$ mm$^2$/min is preferred, while greater than about $2.6 \times 10^{-6}$ mm$^2$/min is more preferred and greater than about $6.4 \times 10^{-6}$ mm$^2$/min is most preferred.

It is known that on-eye movement of the lens is required to ensure good tear exchange, and ultimately, to ensure good corneal health. Ion permeability is one of the predictors of on-eye movement, because the permeability of ions is believed to be directly proportional to the permeability of water.

The present invention is generally directed to a soft contact lens, especially silicone hydrogel contact lens, which has a capability of delivering a hydrophobic comfort agent into the eye of a wearer. The hydrophobic comfort agents, which include without limitation lipids, fatty acids, fatty alcohols, hydrocarbons with $C_{16}$ to $C_{36}$ in length, silicone oils, and mineral oils, released from the soft contact lens when being worn can strengthen and stabilize the tear film lipid layer and thereby can alleviate the dryness of the eye. The present invention is partly based on the discovery that a silicone hydrogel contact lens can have hydrophobic regions on a microscopic scale or hydrophobic components which can sequester a large amount of one or more hydrophobic comfort agents. Those hydrophobic comfort agents in a contact lens of the invention is not susceptible to be released in a lens package containing a buffered aqueous solution. However, it is believed that, when be worn on the eye of a wearer, those hydrophobic comfort agents can be released into the tear film and become building materials for the tear film lipid layer. It is also believed that the primary function of the tear film lipid layer is to retard evaporation of the aqueous layer. By having a stabilized lipid layer, water evaporation can be reduced and symptom of dryness of the eye can be alleviated.

In one aspect, the present invention provides a soft hydrogel contact lens comprising a polymeric matrix and a hydrophobic comfort agent which is not covalently linked to the polymer matrix but distributed therein, wherein the polymeric matrix comprises hydrophobic units derived from a silicone-containing monomer or macromer and/or a hydrophobic monomer and hydrophilic units derived from a hydrophilic monomer or macromer, wherein the soft contact lens is characterized by its capability of gradually releasing the hydrophobic comfort agent from the polymer matrix into the eye of a wearer when being worn.

The term "derived from" in reference to polymeric units (e.g., hydrophobic or hydrophilic units) in the polymer matrix means that the polymeric units are obtained from a specified monomer in a polymerization reaction.

In accordance with the invention, a hydrophobic comfort agent is a compound or a mixture of compounds which can strengthen and/or stabilize the tear film lipid layer. Examples of hydrophobic comfort agents include, without limitation, phospholipids, monoglycerides, diglycerides, triglycerides, glycolipids, glyceroglycolipids, sphingolipids, sphingo-glycolipids, fatty alcohols, hydrocarbons having a $C_{12}$-$C_{28}$ chain in length, wax esters, fatty acids, mineral oils, and silicone oils.

Exemplary phospholipids include, without limitation, lecithin, phosphatidyl ethanolamine, lysolecithin, lysophosphatidylethanolamine, phosphatidylserine, phosphatidyl inositol, sphingomyelin, cephalin, cardiolipin, phosphatidic acid, cerebrosides, dicetyl-phosphate, phosphatidyl-choline, dipalmitoyl-phosphatidylcholine, N-(carbonyl-methoxy-polyethylene glycol-2000)-1,2-distearoyl-sn-glycero-3-phosphoethanolamine sodium salt (L-PEG-2000) and mixtures thereof. Preferred phospholipids are phosphatidylcholine, phosphatidylethanolamine, phosphatidylserine, phosphatidylinositol, sphingomyelin, and mixtures thereof.

Glycolipids are carbohydrate-attached lipids. Exemplary glycolipids include, without limitation, glyceroglycolipids, glycosphingolipids, Gangliosides. Exemplary glyceroglycolipids include, without limitation, Galactolipids, Sulfolipids, and mixtures thereof. Glycosphingolipids are ceramides with one or more sugar residues joined in a β-glycosidic linkage at the 1-hydroxyl position. Gangliosides have at least three sugars, one of which must be sialic acid.

Exemplary sphingolipids include, without limitation, sphingomyelins. Sphingomyelins have a phosphorylcholine or phosphoroethanolamine molecule esterified to the 1-hydroxy group of a ceramide.

Exemplary fatty alcohols include, without limitation, capryl alcohol (1-octanol), 2-ethyl hexanol, pelargonic alcohol (1-nonanol), capric alcohol (1-decanol, decyl alcohol), 1-dodecanol (lauryl alcohol), myristyl alcohol (1-tetradecanol), cetyl alcohol (1-hexadecanol), palmitoleyl alcohol (cis-9-hexadecen-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), ricinoleyl alcohol (12-hydroxy-9-octadecen-1-ol), arachidyl alcohol (1-eicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), Cetearyl alcohol, and mixtures thereof.

Fatty acids can be medium chain fatty acids with alphatic tails of 8 to 14 carbons or long chain fatty acids with alphatic tails of at least 16 carbons). The preferred fatty acids are long chain fatty acids. Exemplary fatty acids include, without limitation, oleic acid, stearic acid, palmytic acid myristic acid, linoleic acid, linolenic acid, arachidic acid, arachadonic acid, myristoleic acid; palmitoleic acid; oleic acid; α-linolenic acid; eicosapentaenoic acid; erucic acid; docosahexaenoic acid; combinations thereof.

A monoglyceride is a glyceride consisting of one fatty acid chain covalently bonded to a glycerol molecule through an ester linkage, and can be broadly divided into two groups; 1-monoacylglycerols and 2-monoacylglycerols, depending on the position of the ester bond on the glycerol moiety. A diglyceride is a glyceride consisting of two fatty acid chains covalently bonded to a glycerol molecule through ester linkages. A triglyceride is glyceride in which the glycerol is esterified with three fatty acids.

In a preferred embodiment of the invention, the hydrophobic comfort agent is a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, a hydrocarbon having a $C_{12}$-$C_{28}$ chain in length, or a mixture thereof.

It should be understood that phospholipids, monoglycerides, diglycerides, triglycerides, glycolipids, glyceroglycolipids, sphingolipids, sphingo-glycolipids, fatty acids, fatty alcohols, and hydrocarbons having a $C_{12}$-$C_{28}$ chain in length can contain an unsaturated carbon-carbon bond.

In accordance with the invention, a soft contact lens is prepared from a lens-forming material as known to a person skilled in the art and the polymer matrix of the soft contact lens includes polymeric units derived from a silicone-containing monomer or macromer and/or a hydrophobic monomer.

Any lens-forming materials can be used in the invention. Lens forming materials that are suitable in the fabrication of contact lenses are illustrated by numerous issued US patents and familiar to those skilled in the art. Preferred lens-forming materials are capable of forming hydrogels. A lens-forming material can comprises at least one member selected from the group consisting of a hydrophilic monomer, a hydrophobic monomer, a macromer, a prepolymer, a crosslinking agent with molecular weight less than 1000 Daltons, and a mixture thereof. A lens-forming material can further include other components, such as an initiator (e.g., a photoinitiator or a thermal initiator), a visibility tinting agent, UV-blocking agent, photosensitizers, and the like. Preferably, a silicone hydrogel lens-forming material used in the present invention comprises a silicone-containing macromer or prepolymer.

Preferably, a silicone hydrogel lens-forming material is used in the invention. The silicone hydrogel lens-forming material comprises at least one silicon-containing monomer, at least one silicone-containing macromer, at least one silicone-containing prepolymer, or a mixture thereof. Alternatively, a silicone hydrogel lens-forming material can be any lens formulations for making silicone hydrogel contact lenses. Exemplary lens formulations include without limitation the formulations of lotrafilcon A, lotrafilcon B, etafilcon A, genfilcon A, lenefilcon A, polymacon, acquafilcon A, balafilcon, senofilcon A, comfilcon A, and the like.

Any monomers suitable for making contact lenses can be used in the invention. Preferably, vinylic monomers are used in the invention.

Examples of silicone-containing monomers include: without limitation, 3-methacryloxy propylpentamethyldisiloxane; bis(methacryloxypropyl)tetramethyl-disiloxane; N-[tris(trimethylsiloxy)silylpropyl]acrylamide; N-[tris (trimethylsiloxy)silylpropyl]methacrylamide, and tristrimethylsilyloxysilylpropyl methacrylate (TRIS); N-[tris(trimethylsiloxy)silylpropyl]methacrylamide ("TSMAA"); N-[tris(trimethylsiloxy)-silylpropyl]acrylamide ("TSAA"); (3-methacryloxy-2-hydroxypropyloxy)propylbis(trimethylsiloxy) methylsilane); (3-methacryloxy-2-hydroxypropyloxy)propyltris(trimethylsiloxy)silane; 3-methacryloxy-2-(2-hydroxyethoxy)propyloxy)propylbis(trimethylsiloxy) methylsilane; N-2-methacryloxyethyl-O-(methyl-bis-trimethylsiloxy-3-propyl)silyl carbamate; silicone-containing vinyl carbonate or vinyl carbamate monomers, e.g., 1,3-bis[4-vinyloxycarbonyloxy)but-1-yl]tetramethyl-disiloxane, 3-(trimethylsilyl)-propyl vinyl carbonate, 3-(vinyloxycarbonylthio)propyl-[tris(trimethylsiloxy)silane], 3-[tris(trimethylsiloxy)silyl] propylvinyl carbamate, 3-[tris (trimethylsiloxy)silyl] propyl allyl carbamate, 3-[tris(trimethylsiloxy)silyl]propyl vinyl carbonate, t-butyldimethylsiloxyethyl vinyl carbonate, trimethylsilylethyl vinyl carbonate, and trimethylsilylmethyl vinyl carbonate; monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy)propyl terminated, mono-butyl terminated polydimethylsiloxane); dimethacrylated or diacrylated polydimethylsiloxanes of various molecular weight; vinyl terminated polydimethylsiloxanes; vinyl terminated polydimethylsiloxanes of various molecular weight; methacrylamide-terminated polydimethylsiloxanes; acrylamide-terminated polydimethylsiloxanes; acrylate-terminated polydimethylsiloxanes; methacrylate-terminated polydimethylsiloxanes; bis-3-methacryloxy-2-hydroxypropyloxypropyl polydimethylsiloxane; N, N, N',N'-tetrakis(3-methacryloxy-2-hydroxypropyl)-alpha,omega-bis-3-aminopropyl-polydimethylsiloxane; polysiloxanylalkyl (meth) acrylic monomers; siloxane-containing macromer selected from the group consisting of Macromer A, Macromer B, Macromer C, and Macromer D described in U.S. Pat. No. 5,760,100 (herein incorporated by reference in its entirety); the reaction products of glycidyl methacrylate with amino-functional polydimethylsiloxanes; hydroxyl-functionalized siloxane-containing monomers or macromers; siloxane-containing macromers disclosed in U.S. Pat. No. 6,762,264 (here incorporated by reference in its entirety). Di and triblock macromers consisting of polydimethylsiloxane and polyakyleneoxides could also be of utility. For example one might use methacrylate end capped polyethyleneoxide-block-polydimethylsiloxane-block-polyethyleneoxide to enhance oxygen permeability. Suitable monofunctional hydroxyl-functionalized siloxane-containing monomers and suitable multifunctional hydroxyl-functionalized siloxane-containing monomers are commercially available from Gelest, Inc, Morrisville, Pa.

Nearly any hydrophilic monomer that can be used in making hydrogel contact lenses can be used in the invention. Among the preferred hydrophilic monomers are N,N-dimethylacrylamide (DMA), 2-hydroxyethylmethacrylate (HEMA), hydroxyethyl acrylate, hydroxypropyl acrylate, hydroxypropyl methacrylate (HPMA), trimethylammonium 2-hydroxy propylmethacrylate hydrochloride, dimethylaminoethyl methacrylate (DMAEMA), dimethylaminoethylmethacrylamide, acrylamide, methacrylamide, allyl alcohol, vinylpyridine, glycerol methacrylate, N-(1,1dimethyl-3- oxobutyl)acrylamide, N-vinyl-2-pyrrolidone (NVP), acrylic acid, methacrylic acid, N-vinyloxycarbonyl-L-alanine, N-vinyl formamide, N-vinyl acetamide, N-vinyl isopropylamide, N-vinyl-N-methyl acetamide, allyl alcohol, and N-vinyl caprolactam.

Nearly any hydrophobic monomer that can be used in making contact lenses can be used in the invention. Examples of hydrophobic monomers include without limitation silicone-containing vinylic monomers, $C_1$-$C_{18}$-alkylacrylates and -methacrylates, $C_3$-$C_{18}$ alkylacrylamides and -methacrylamides, acrylonitrile, methacrylonitrile, vinyl-$C_1$-$C_{18}$-alkanoates, $C_2$-$C_{18}$-alkenes, $C_2$-$C_{18}$-halo-alkenes, styrene, $C_1$-$C_6$-alkylstyrene, vinylalkylethers in which the alkyl moiety has 1 to 6 carbon atoms, $C_2$-$C_{10}$-perfluoroalkylacrylates and -methacrylates or correspondingly partially fluorinated acrylates and methacrylates, $C_3$-$C_{12}$-perfluoralkyl-ethyl-thiocarbonylaminoethyl-acrylates and -methacrylates, and acryloxy and methacryloxy-alkylsiloxanes. Preferred hydrophobic monomers include without limitation methylacrylate, ethyl-acrylate, propylacrylate, isopropylacrylate, cyclohexylacrylate, tert-butyl methacrylate, isobonyl methacrylate, 2-ethylhexylacrylate, methylmethacrylate, ethylmethacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, and hexafluorobutyl methacrylate.

Any actinically crosslinkable prepolymers can be used in the invention. Examples of actinically crosslinkable prepolymers include, but are not limited to, a water-soluble crosslinkable poly(vinyl alcohol) prepolymer described in U.S. Pat. Nos. 5,583,163 and 6,303,687 (incorporated by reference in their entireties); a water-soluble vinyl group-terminated polyurethane prepolymer described in U.S. Patent Application Publication No. 2004/0082680 (herein incorporated by reference in its entirety); derivatives of a polyvinyl alcohol, polyethyleneimine or polyvinylamine, which are disclosed in U.S. Pat. No. 5,849,841 (incorporated by reference in its entirety); a water-soluble crosslinkable polyurea prepolymer described in U.S. Pat. No. 6,479,587 and in U.S. Published Application No. 2005/0113549 (herein incorporated by reference in their entireties); crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635 and U.S. Pat. No. 6,492,478; branched polyalkylene glycolurethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; crosslinkable polyallylamine gluconolactone prepolymers disclosed in International Application No. WO 2000/31150 and U.S. Pat. No. 6,472,489, and actinically-crosslinkable silicone-containing prepolymers.

Any suitable actinically-crosslinkable silicone-containing prepolymer can be used in the invention. Preferably, a silicone-containing prepolymer comprises hydrophilic segments and hydrohpobic segments. Examples of silicone-containing prepolymers are those described in commonly-owned U.S. Pat. Nos. 6,039,913, 7,091,283, 7,268,189 and 7,238,750, and U.S. patent application Ser. Nos. 09/525,158, 11/825,961, 12/001,562, 12/001,521, 12/077,773, 12/077,772, which are incorporated herein by references in their entireties.

The lens-forming material can comprise one or more crosslinking agents (i.e., compounds with two or more acryl groups or three or more thiol or ene-containing groups and with molecular weight less than 700 Daltons). Examples of preferred vinylic crosslinkers include without limitation methylenebisacrylamide, methylenebismethacrylamide, ethyleneglycol dimethacylate (EGDMA), dienthylene glycol dimethacrylate, tetraethyleneglycol dimethacrylate (TEGDMA), triethyleneglycol dimethacrylate (TrEGDMA), polyethylene glycol dimethacrylate, ethyleneglycol diacylate, dienthylene glycol diacrylate, tetraethyleneglycol diacrylate, triethyleneglycol diacrylate, polyethylene glycol diacrylate, triallyl isocyanurate, ethylenediamine dimethyacrylamide, glycerol dimethacrylate, and combinations thereof.

In accordance with the present invention, a lens-forming material can be a solution or a solvent-free liquid or melt at a temperature below about 80° C. A person skilled in the art will known well how to prepare silicone hydrogel lens-forming material.

For example, a solution can be prepared by dissolving a lens-forming material in any suitable solvent known to a person skilled in the art. Examples of suitable solvents include without limitation water, alcohols, such as $C_1$-$C_{14}$ alkanols (preferred examples: ethanol, methanol, 1-propanol, isopropanol, 2-butanol, menthol, cyclohexanol, cyclopentanol, exo-norborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl alcohol, 2-methyl-2-pentanol, 2,3-dimethyl-2-butanol, 3-methyl-3-pentanol, 1-methylcylohexanol, 2-methyl-2-hexanol, 3,7-dimethyl-3-octanol, 1-chloro-2-methyl-2-propanol, 2-methyl-2-heptanol, 2-methyl-2-octanol, 2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-ethyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol, 2,3,4-trimethyl-3-pentanol, 3,7-dimethyl-3-octanol, 2-phenyl-2-butanol, 2-methyl-1-phenyl-2-propanol or 3-ethyl-3-pentanol), carboxylic acid amides (e.g., dimethylformamide), dipolar aprotic solvents (e.g. dimethyl sulfoxide, methyl ethyl ketone), ketones (e.g., acetone, butanone, or cyclohexanone), hydrocarbons (e.g., toluene, ethers, THF, dimethoxyethane or dioxane), and halogenated hydrocarbons (e.g., trichloroethane), mixtures of water with an alcohol, mixture of water with one or more organic solvents, and mixtures of two or more organic solvents.

It must be understood that a lens-forming material can also comprise various components, such as, for example, polymerization initiators (e.g., photoinitiator or thermal initiator), a visibility tinting agent (e.g., dyes, pigments, or mixtures thereof), UV-blocking (absorbing) agent, photosensitizers, inhibitors, antimicrobial agents (e.g., preferably silver nanoparticles or stabilized silver nanoparticles), bioactive agent, leachable lubricants, fillers, and the like, as known to a person skilled in the art.

These antimicrobial agents (e.g., preferably silver nanoparticles or stabilized silver nanoparticles) should be incorporated in resultant contact lenses so as to impart the resultant contact lenses antimicrobial properties.

A "leachable wetting agent" is intended to describe a wetting material that is not covalently attached to the polymer matrix of a resultant contact lens but instead is physically entrapped in the polymer matrix of the resultant lens. Any non-crosslinkable hydrophilic polymers can be used as leachable wetting agent in the invention. Exemplary non-crosslinkable hydrophilic polymers include, but are not limited to, polyvinylalcohols (PVAs); polyethylene oxide; polyethylene-polypropylene block copolymers; polyamides; polyimides; polylactone; a homopolymer of N-vinylpyrrolidone (e.g., polyvinylpyrrolidone, PVP); a copolymer of N-vinylpyrrolidone and one or more hydrophilic vinylic monomers described above; a homopolymer of acrylamide or methacrylamide; a copolymer of acrylamide or methacrylamide with one or more hydrophilic vinylic monomers described above; a homopolymer of N-vinyl formamide, N-vinyl acetamide, N-vinyl isopropylamide, or N-vinyl-N-methyl acetamide, a copolymer of N-vinyl formamide, N-vinyl acetamide, N-vinyl isopropylamide, or N-vinyl-N-methyl acetamide with one or more hydrophilic vinylic monomers described above, and mixtures thereof.

The number-average molecular weight $M_n$ of the non-crosslinkable hydrophilic polymer is preferably from 20,000 to 500,000, more preferably from 30,000 to 100,000, even more preferably from 35,000 to 70,000.

A combination of hydrophobic comfort agent and a leachable wetting agent may provide even greater benefits by addressing both the aqueous and lipid layers of the tear film.

Initiators, for example, selected from materials well known for such use in the polymerization art, may be included in the lens-forming material in order to promote, and/or increase the rate of, the polymerization reaction. An initiator is a chemical agent capable of initiating polymerization reactions. The initiator can be a photoinitiator or a thermal initiator.

A photoinitiator can initiate free radical polymerization and/or crosslinking by the use of light. Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is azobisisobutyronitrile (AIBN).

Examples of preferred pigments include any colorant permitted in medical devices and approved by the FDA, such as D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, etc. See Marmiom DM Handbook of U.S. Colorants for a list of colorants that may be used with the present invention. A more preferred embodiment of a pigment include (C.I. is the color index no.), without limitation, for a blue color, phthalocyanine blue (pigment blue 15:3, C.I. 74160), cobalt blue (pigment blue 36, C.I. 77343), Toner cyan BG (Clariant), Permajet blue B2G (Clariant); for a green color, phthalocyanine green (Pigment green 7, C.I. 74260) and chromium sesquioxide; for yellow, red, brown and black colors, various iron oxides; PR122, PY154, for violet, carbazole violet; for black, Monolith black C-K (CIBA Specialty Chemicals).

A contact lens of the invention has an oxygen permeability of preferably at least about 40 barrers, more preferably at least about 60 barrers, even more preferably at least about 80 barrers. In accordance with the invention, an oxygen permeability is an apparent (directly measured when testing a sample with a thickness of about 100 microns) oxygen permeability according to procedures described in Examples.

A contact lens of the invention has an elastic modulus of from about 0.2 MPa to about 2.0 MPa, preferably from about 0.3 MPa to about 1.5 MPa, more preferably from about 0.4 MPa to about 1.2, even more preferably from about 0.5 MPa to about 1.0 MPa.

A contact lens of the invention has an Ionoflux Diffusion Coefficient, D, of, preferably at least about $1.5 \times 10^{-6}$ mm$^2$/min, more preferably at least about $2.6 \times 10^{-6}$ mm$^2$/min, even more preferably at least about $6.4 \times 10^{-6}$ mm$^2$/min.

A contact lens of the invention further has a water content of preferably from about 15% to about 70%, more preferably from about 20% to about 55% by weight when fully hydrated. The water content of a silicone hydrogel contact lens can be measured according to Bulk Technique as disclosed in U.S. Pat. No. 5,849,811.

A contact lens of the invention has a surface hydrophilicity characterized by having an averaged water contact angle of about 90 degrees or less, preferably about 80 degrees or less, more preferably about 70 degrees or less, more preferably about 60 degrees or less. Such lens surface hydrophilicity can be achieved by using one of the surface modification methods described above.

In another aspect, the present invention provides an ophthalmic product comprising a sealed package which include a packaging solution and a soft hydrogel contact lens, wherein the hydrogel contact lens comprises a polymer matrix and a hydrophobic comfort agent which is not covalently linked to the polymer matrix but distributed therein, wherein the polymeric matrix comprises hydrophobic units derived from a silicone-containing monomer or macromer and/or a hydrophobic monomer and hydrophilic units derived from a hydrophilic monomer or macromer, wherein the hydrogel contact lens has a capability of gradually releasing the hydrophobic comfort agent during wear over at least about 4 hours after storing in the packaging solution for at least about one month.

All of the various embodiments of soft hydrogel contact lens, lens-forming materials, and hydrophobic comfort agent described above can be used in this aspect of the invention.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes) prior to dispensing to users. A person skilled in the art will understand well how to seal and sterilize lens packages.

In accordance with the present invention, a packaging solution is ophthalmically compatible, meaning that a contact lens treated with the solution is generally suitable and safe for direct placement on the eye without rinsing, that is, the solution is safe and comfortable for contact with the eye via a contact lens that has been wetted with the solution. A packaging solution of the invention may be any water-based solution that is used for the storage of contact lenses. Typical solutions include, without limitation, saline solutions, other buffered solutions, and deionized water. The preferred aqueous solution is saline solution containing salts including one or more other ingredients known to a person skilled in the art. Examples of other ingredients include without limitation, suitable buffer agents, tonicity agents, water-soluble viscosity builders, surfactants, antibacterial agents, preservatives, and lubricants (e.g., cellulose derivatives, polyvinyl alcohol, polyvinyl pyrrolidone).

The preferred packaging solution of the invention contains a viscosity-enhancing polymer. The viscosity-enhancing polymer preferably is nonionic. Increasing the solution viscosity provides a film on the lens which may facilitate comfortable wearing of the contact lens. The viscosity-enhancing component may also act to cushion the impact on the eye surface during insertion and serves also to alleviate eye irritation.

Preferred viscosity-enhancing polymers include, but are not limited to, water soluble cellulose-derived polymers, water-soluble polyvinylalcohols (PVAs), high molecular weight poly(ethylene oxide) having a molecular weight greater than about 2000 (up to 10,000,000) Daltons, polyvinylpyrrolidone with a molecular weight of from about 30,000 Daltons to about 1,000,000 Daltons, a copolymer of at least one vinyl lactam with one or more hydrophilic monomers, and the like. Water soluble cellulose-derived polymers are most preferred viscosity-enhancing polymers. Examples of useful cellulose-derived polymers include without limitation cellulose ethers.

Exemplary preferred cellulose ethers are methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof. More preferably, a cellulose ether is hydroxyethyl cellulose (HEC), hydroxypropylmethyl cellulose (HPMC), and mixtures thereof.

The viscosity-enhancing polymer is present in the composition in an amount of from about 0.01% to about 5% by weight, preferably from about 0.05% to about 3% by weight, even more preferably from about 0.1% to about 1% by weight, based on the total amount of the packaging solution.

Any copolymers of vinylpyrrolidone and at least one hydrophilic monomer can be used in this invention. A preferred class of polyvinylpyrrolidone copolymers are the copolymers of vinyloyrrolidone and at least one amino-containing vinylic monomer. Examples of amino-containing vinylic monomers include without limitation alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, N-vinylalkylamide having 3-10 carbon atoms. Examples of preferred N-vinyl alkylamide include without limitation N-vinyl formaide, N-vinyl acetamide, N-vinyl isopropylamide, and N-vinyl-N-methyl acetamide. Such preferred copolymers are commercially available, e.g., Copolymer 845 and Copolymer 937 from ISP.

A packaging solution of the invention has a viscosity of from 1.5 centipoise to about 20 centipoise at 25° C., preferably from about 2.0 centipoise to about 15 centipoise at 25° C., more preferably from about 2.0 centipoise to about 8 centipoise at 25° C.

In accordance with the invention, the packaging solution comprises a polyethylene glycol having a molecular weight of 2000 or less, preferably 1000 or less, even more preferably 600 or less, most preferably from about 100 to about 500 Daltons.

In a preferred embodiment of the invention, the packaging solution comprises an α-oxo-multi-acid or salt thereof in an amount sufficient to have a reduced susceptibility to oxidation degradation of the polyethylene glycol in the packaging solution. A commonly-owned co-pending patent application (US patent application publication No. 2004/0116564 A1, incorporated herein in its entirety) discloses that oxo-multi-acid or salt thereof can reduce the susceptibility to oxidative degradation of a PEG-containing polymeric material.

Exemplary α-oxo-multi-acids or biocompatible salts thereof include without limitation citric acid, 2-ketoglutaric acid, or malic acid or biocompatible (preferably ophthalmically compatible) salts thereof. More preferably, an α-oxo-multi-acid is citric or malic acid or biocompatible (preferably ophthalmically compatible) salts thereof (e.g., sodium, potassium, or the like).

The packaging solution of the present invention preferably contains a buffering agent. The buffering agents maintain the pH preferably in the desired range, for example, in a physiologically acceptable range of about 6 to about 8. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis (2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis (2-ethanesulfonic acid), TES (N-[Tris(hydroxymethyl) methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis (tris[hydroxymethyl]-methylamino)propane (bis-TRIS-propane). The amount of each buffer agent is that amount necessary to be effective in achieving a pH of the composition of from about 6.0 to about 8.0. Typically, it is present in an amount of from 0.001% to 2%, preferably from 0.01% to 1%; most preferably from about 0.05% to about 0.30% by weight.

The packaging solutions according to the invention are preferably formulated in such a way that they are isotonic with the lacrimal fluid. A solution which is isotonic with the lacrimal fluid is generally understood to be a solution whose concentration corresponds to the concentration of a 0.9% sodium chloride solution (308 mOsm/kg). Deviations from this concentration are possible throughout; if desired.

The isotonicity with the lacrimal fluid, or even another desired tonicity, may be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

In accordance with the invention, the solution can further comprises mucin-like materials, ophthalmically beneficial materials, and/or surfactants.

Exemplary mucin-like materials include without limitation polyglycolic acid, polylactides, and the likes. A mucin-like material can be used as guest materials which can be released continuously and slowly over extended period of time to the ocular surface of the eye for treating dry eye syndrome. The mucin-like material preferably is present in effective amounts.

Exemplary ophthalmically beneficial materials include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Surfactants can be virtually any ocularly acceptable surfactant including non-ionic, anionic, and amphoteric surfactants. Examples of preferred surfactants include without limitation poloxamers (e.g., Pluronic® F108, F88, F68, F68LF, F127, F87, F77, P85, P75, P104, and P84), poloamines (e.g., Tetronic® 707, 1107 and 1307, polyethylene glycol esters of fatty acids (e.g., Tween® 20, Tween® 80), polyoxyethylene or polyoxypropylene ethers of 012-018 alkanes (e.g., Brij® 35), polyoxyethyene stearate (Myrj® 52), polyoxyethylene propylene glycol stearate (Atlas® G 2612), and amphoteric surfactants under the trade names Mirataine® and Miranol®.

The present invention, in a further aspect, provides a process for making a soft contact lens capable of gradually delivering a hydrophobic comfort agent during wearing of the contact lens. The method of the invention comprises the steps of: a) dipping a soft hydrogel contact lens in a solution containing a hydrophobic comfort agent and an organic solvent miscible with water, wherein the soft hydrogel contact lens comprises a polymer matrix including polymeric units derived from a silicone-containing monomer or macromer and/or a hydrophobic monomer, wherein the organic solvent swells the soft hydrogel contact so as to allow the hydrophobic comfort agent to be incorporate into the polymer matrix of the soft hydrogel contact lens; b) hydrating the soft hydrogel contact lens comprising the comfort agent distributed therein in water or a buffered aqueous solution; and c) placing and sealing the hydrated soft hydrogel contact lens in a lens package containing a packaging solution.

All of the various embodiments of the soft hydrogel contact lens, lens-forming materials, hydrophobic comfort agent, lens packages, and packaging solutions described above can be used in this aspect of the invention.

The present invention, in still a further aspect, provides a method for making a soft contact lens capable of gradually delivering a hydrophobic comfort agent during wearing of the contact lens. The method of the invention comprises the steps of: a) obtaining a fluid prepolymer composition comprising a first organic solvent, an actinically-crosslinkable lens-forming material, and a hydrophobic comfort agent, wherein the actinically-crosslinkable lens-forming material comprises actinincally-crosslinkable groups and can be polymerized thermally or actinically to form the polymer matrix of the soft contact lens, wherein the actinically-crosslinkable lens-forming material comprises monomer, macromer, and/or prepolymer, wherein the hydrophobic comfort agent is free of any actinically-crosslinkable group; b) introducing an amount of the fluid prepolymer composition in a mold for making a contact lens; c) polymerizing the actinically-crosslinkable prepolymer in the mold to form the soft contact lens with the hydrophobic comfort agent being not covalently linked to the polymer matrix but being distributed therein in a substantially uniform manner; d) hydrating the resultant soft contact lens in water or an aqueous solution to replace the first organic solvent with water or the aqueous solution; e) packaging the hydrated soft contact lens in a container containing a packaging solution; and f) sterilizing the soft contact lens in the package, wherein the sterilized soft contact lens is capable of gradually releasing the hydrophobic comfort agent during wear, provided that the method is free of any extraction step with a second organic solvent.

All of the various embodiments of the soft hydrogel contact lens, lens-forming materials, hydrophilic monomer, hydrophobic monomers, silicone-containing monomers, silicone-containing macromers, silicone-containing prepolymers, hydrophobic comfort agents, lens packages, non-crosslinkable hydrophilic polymers, and packaging solutions described above can be used in this aspect of the invention.

In accordance with the invention, the lens-forming material can be introduced (dispensed) into a cavity formed by a mold according to any known methods.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for preparing ocular lenses. For example, polymeric materials, such as polyethylene, polypropylene, polystyrene, PMMA, cyclic olefin copolymers (e.g., Topas® COC from Ticona GmbH of Frankfurt, Germany and Summit, N.J.; Zeonex® and Zeonor® from Zeon Chemicals LP, Louisville, Ky.), or the like can be used.

Other materials that allow UV light transmission could be used, such as quartz, glass, CaF$_2$, and sapphire.

In a preferred embodiment, when the lens-forming material is composed essentially of prepolymers (i.e., substantially free of monomers and crosslinking agent having a molecular weight of less than 700 Daltons), reusable molds can be used. Examples of reusable molds made of quartz or glass are those disclosed in U.S. Pat. No. 6,627,124, which is incorporated by reference in their entireties. In this aspect, the lens-forming material is poured into a mold consisting of two mold halves, the two mold halves not touching each other but having a thin gap of annular design arranged between them. The gap is connected to the mold cavity, so that excess lens-forming material can flow into the gap. Instead of polypropylene molds that can be used only once, it is possible for reusable quartz, glass, sapphire molds to be used, since, following the production of a lens, these molds can be cleaned rapidly and effectively to remove unreacted materials and other residues, using water or a suitable solvent, and can be dried with air. Reusable molds can also be made of a cyclic olefin copolymer, such as for example, Topas® COC grade 8007-S10 (clear amorphous copolymer of ethylene and norbornene) from Ticona GmbH of Frankfurt, Germany and Summit, N.J., Zeonex® and Zeonor0 from Zeon Chemicals LP, Louisville, Ky. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual mold faces, damage as a result of contact is ruled out. This ensures a high service life of the molds, which, in particular, also ensures high reproducibility of the contact lenses to be produced and high fidelity to the lens design.

After the lens-forming material is dispensed into the mold, it is polymerized to produce a contact lens. Crosslinking may be initiated in the mold e.g. by means of actinic radiation, such as UV irradiation, ionizing radiation (e.g., gamma or X-ray irradiation). Where the polymerizable components in the lens-forming material are essentially prepolymers, the mold containing the lens-forming material can be exposed to a spatial limitation of actinic radiation to crosslink the prepolymers.

The crosslinking according to the invention may be effected in a very short time, e.g. in ≤60 minutes, advantageously in ≤20 minutes, preferably in ≤10 minutes, most preferably in ≤5 minutes, particularly preferably in 1 to 60 seconds and most particularly in 1 to 30 seconds.

Opening of the mold so that the molded article can be removed from the mold may take place in a manner known per se.

If the molded contact lens is produced solvent-free from an already purified prepolymer according to the invention, then after removal of the molded lens, it is not normally necessary to follow up with purification steps such as extraction. This is because the prepolymers employed do not contain any undesired constituents of low molecular weight; consequently, the crosslinked product is also free or substantially free from such constituents and subsequent extraction can be dispensed with. Accordingly, the contact lens can be directly transformed in the usual way, by hydrolysis and hydration, into a ready-to-use contact lens. Appropriate embodiments of hydration are known to the person skilled in the art, whereby ready-to-use contact lenses with very varied water content may be obtained. The contact lens is expanded, for example, in water, in an aqueous salt solution, especially an aqueous salt solution having an osmolarity of about 200 to 450 milli-osmole in 1000 ml (unit: mOsm/ml), preferably about 250 to 350 mOsm/l and especially about 300 mOsm/l, or in a mixture of water or an aqueous salt solution with a physiologically compatible polar organic solvent, e.g. glycerol. Preference is given to expansions of the article in water or in aqueous salt solutions.

If the molded contact lens is produced from a solution of an already purified prepolymer according to the invention, then the crosslinked product also does not contain any troublesome impurities. It is therefore not necessary to carry out subsequent extraction. The contact lenses obtained by this process are subject to hydrolysis and hydration processes.

Similarly, if the molded contact lens is produced from a solvent solution of an already purified prepolymer according to the invention, it is not necessary to carry out subsequent extraction, but instead of hydration process to replace the solvent.

The molded contact lenses can further subject to further processes, such as, for example, surface treatment, sterilization, and the like.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Oxygen permeability measurements. The oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm$^3$/min., while a nitrogen stream is passed on the opposite side of the lens at a rate of about 10 to 20 cm$^3$/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, P$_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, Dk$_{app}$, (barrers) is determined from the following formula:

$$Dk_{app} = Jt/(P_{oxygen})$$

where J=oxygen flux [microliters $O_2/cm^2$–minute]; $P_{oxygen}$= ($P_{measured}$–$P_{water}$ vapor)=(% $O_2$ in air stream) [mm Hg]=partial pressure of oxygen in the air stream; $P_{measured}$=barometric pressure (mm Hg); $P_{water}$ vapor=0 mm Hg at 34° C. (in a dry cell) (mm Hg); $P_{water}$ vapor=40 mm Hg at 34° C. (in a wet cell) (mm Hg); and t=average thickness of the lens over the exposed test area (mm). The oxygen transmissibility (Dk/t) of the material may be calculated by dividing the oxygen permeability ($Dk_{app}$) by the average thickness (t) of the lens.

Ion Permeability Measurements. The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of $0.314 \times 10^{-3}$ $mm^2$/minute.

Example 2

Synthesis of Chain-Extended PDMS-dimethacrylate

In the first step, α,ω-bis(2-hydroxyethoxypropyl)-polydimethylsiloxane (Mn=2000, Shin-Etsu, KF-6001a) is capped with isophorone diisocyanate by reacting 49.85 g of α,ω-bis(2-hydroxyethoxypropyl)-polydimethylsiloxane with 11.1 g isophorone diisocyanate (IPDI) in 150 g of dry methyl ethyl ketone in the presence of 0.063 g of dibutyltindilaurate (DBTDL). The reaction is kept for 4.5 hours at 40° C., forming IPDI-PDMS-IPDI. In the second step, a mixture of 164.8 g of α,ω-bis(2-hydroxyethoxypropyl)-polydimethylsiloxane (Mn=3000, Shin-Etsu, KF-6002) and 50 g of dry methyl ethyl ketone are added dropwise to the IPDI-PDMS-IPDI solution to which is added an additional 0.063 g of DBTDL. The reactor is held for 4.5 hours at 40° C., forming HO-PDMS-IPDI-PDMS-IPDI-PDMS-OH. MEK is then removed under reduced pressure. In the third step, the terminal hydroxyl-groups are capped with methacryloyloxyethyl groups in a third step by addition of 7.77 g of isocyanatoethylmethacrylate (IEM) and an additional 0.063 g of DBTDL, forming IEM-PDMS-IPDI-PDMS-IPDI-PDMS-IEM.

Example 3

A lens formulation is prepared by mixing 31.5% by weight of polydimethylsiloxane macromer prepared in Example 2, 20.5% by weight of TRIS-acrylamide (ShinEtsu #805001); 23% by weight of DMA (Dimethylacrylamide); 0.5% by weight of N-(carbonyl-methoxypolyethylene glycol-2000)-1,2-distearoyl-sn-glycero-3-phosphoethanolamine sodium salt (L-PEG-2000), 1.0% by weight of Darocur 1173, 0.1% by weight of Cu phthalocyanine dispersion (5%, in TRIS methacrylate), and 23.4% by weight of 1-propanol.

The lens formulation is dispensed onto a female mold half by using an EFD automatic dispenser. The female mold half is then mated with a corresponding male mold half. The mold is closed by using a pneumatic closing system. The formulation is UV cured under 2 different UV lights (1.8 $mW/cm^2$ each) for total exposure time of about 30 seconds.

Lenses are demolded and extracted with an organic solvent (e.g., isopropanol, 1-propanol, Dowanol, methyl ethyl ketone (MEK), or the like) and then dipped in a Dowanol PM (or alternatively MEK or 1-propanol) solution of polyacrylic acid (0.1% by weight, pH ~2.0). The lenses are then rinsed for 60 seconds in water and then dipped in a Dowanol (or alternatively MEK or 1-propanol) solution of 1,2-dimyristoyl-sn-glycero-3-phosphocholine (DMPC, 1%) for about 60 to about 100 seconds. The lenses are then rinsed in water for 120 seconds and packaged in PBS. Lenses are then autoclaved for 30 min at 121° C.

Example 4

Lenses (as prepared in Example 3) are subjected to one of two release tests in artificial tear fluid (ATF) prepared without any phospholipids and having a composition shown in Table 1.

TABLE 1

| Component | Concentration |
| --- | --- |
| lysozyme | 2.2 mg/ml |
| lactoferrin | 2.3 mg/ml |
| albumin | 28.6 µg/ml |
| mucin | 0.1 mg/ml |
| lipocalin (TSP)/β-lactoglobulin | 1.5 mg/ml |
| cholesterol | 1.75 µg/ml |
| cholesterol oleate (esters) | 18.6 µg/ml |
| purified water | 980 ml |
| sodium chloride | 8 g/L |
| sodium dihydrogen phosphate (monobasic) | 0.2848 g/L |
| sodium phosphate | 2.127 g/L |

The first test is designed to maximize release of DMPC from the lens by refreshing the ATF frequently. A single lens is placed in 500 µL of ATF and incubated at 35° C. for 8 hrs. Every 30 min, the sample is vortexed, the ATF is withdrawn, a fresh 500 µL aliquot of ATF is added to the lens, the sample is again vortexed, and the sample is returned to the incubator. At the conclusion of 8 hrs, the lenses are removed from ATF, placed in 1 mL clean PBS, and submitted for analysis of DMPC content.

The second test is designed to try to maximize the amount of DM PC in ATF by leaving the lens in ATF for the entire release test. A single lens is placed in 1 mL ATF and incubated at 35° C. for 8 hrs. Every 30 min, the sample is vortexed and then returned to the incubator. At the conclusion of 8 hrs, the lens is removed from the ATF and the ATF is submitted for analysis. All analysis is done using an enzymatic assay method.

A control set of lenses is submitted to confirm loading of the lenses with DMPC. This control sample set (n=5) show an average loading of 200 µg DMPC per lens.

The set of lenses released according to the first test (frequent replacement of the ATF during release) shows an average DMPC content of 177 µg DMPC per lens (n=5).

Three ATF samples are pooled to increase the DMPC signal. The test for 3 pooled samples shows presence of DMPC in the ATF equivalent to 6 µg DM PC per lens. The value for the 3 pooled samples is just below the dynamic range of the assay, making confidence in the quantified DMPC levels difficult yet still providing evidence of DMPC release from the lenses.

Example 5

Lenses are prepared according to the procedures described in Example 3, except that DMPC used in this example is a radio labeled DMPC (C14). The radio labeled DMPC is supplied by New England Nuclear (Waltham, Mass.). Lenses are loaded with radio-labeled DMPC by dipping the lenses into a solution of the radio-labeled DMPC in 1-propanol. Loaded lenses are then subjected to release testing using artificial tear fluid (ATF) as the release media. The ATF composition is shown in Table 2. Components listed in Table 2 are dissolved in a phosphate buffered saline solution to provide a physiologically acceptable pH and osmolality.

TABLE 2

| Component | Concentration [mg/mL] |
| --- | --- |
| Lysozyme | 2.2 |
| Lactoferrin | 2.3 |
| Albumin | 0.0286 |
| Mucin | 0.1 |
| Lipocalin (TSP)/β-lactoglobulin | 1.5 |
| Cholesterol | 0.00175 |
| Cholesterol oleate (esters) | 0.0186 |
| Phosphatidylethanolamine | 0.0005 |
| Phosphatidylcholine | 0.0011 |

Release tests are conducted by placing a single lens in 1 mL of ATF and then incubating the sample for 24 hours. At specified time points of 0, 2, 4, 10, and 24 hours, small samples of release media are pulled and analyzed for DM PC content using a scintillation counter (C14 emits a weak beta particle).

The DMPC content of the lenses is also measured using one of two techniques:
(1) Lenses that had previously been subjected to release testing are fully extracted and the eluate is then analyzed for DMPC content. This amount of DMPC is numerically added to the DMPC already quantified in the release media. Thus, all DMPC is accounted for, cradle-to-grave.
(2) Other lenses, not subject to release testing, are also extracted to determine initial DMPC content (total loading of DM PC in lenses).

Total DMPC content of the lenses are estimated to be 32.1±2.7 micrograms of DMPC per lens. DMPC content in the ATF release media increase over the entire duration of the release testing. All eight tested samples show release with good reproducibility. The average cumulative DMPC release from the lens is 1.3 µg over the 24-hour test period. DMPC release appears to be first order, indicating a diffusion controlled release mechanism.

Example 6

A lens formulation is prepared as detailed in Example 3 where 1,2-dimyristoyl-sn-glycero-3-phosphocholine (DMPC) is added to the formulation at a concentration of 0.75% by weight and where the formulation solvent, 1-propanol, is reduced to 22.65% by weight. Lens curing is as described in Example 3.

The lenses are demolded and then extracted in methyl ethyl ketone followed by a rinse in DI water for 56 seconds. The lenses are then dipped in a solution of polyacrylic acid (0.36% wt/vol in 1-propanol, pH-2). The lenses are then rinsed in water for 120 seconds and packaged in phosphate buffered saline. Lenses are then autoclaved for 30 minutes at 121° C.

The content of comfort agents, DMPC and L-PEG, are determined as follows. Lenses are exhaustively extracted in isopropanol and the extract is tested for DMPC and N-(carbonyl-methoxypolyethylene glycol-2000)-1,2-disteaoyl-sn-glycero-3-phosphoethanolamine, sodium salt (L-PEG-2000) content. Lenses contain on average 30 µg DMPC and 10 µg L-PEG-2000 per lens.

The release profile of contact lenses with comfort agents (DMPC and L-PEG) are determined as follows. Lenses are placed in release media (artificial tear fluid (ATF) as described in Example 4) for release testing. Lenses are pooled (35 lenses in 3.5 mL ATF and 50 lenses in 5 mL ATF) and then gently agitated at 37° C. for 24 hours. At the conclusion of the 24-hour release study, the lenses are removed from the ATF. The remaining ATF is then transferred to centrifuge tubes and dried overnight under vacuum in a centrifugal evaporator.

The dried residue from the ATF is then resuspended in 1-propanol (1 mL 1-propanol for each original 5 mL ATF) using sonication to assist in resuspension. The resulting solution is analyzed for presence of DMPC using HPLC.

The two samples test positive for presence of DM PC equivalent to 0.48 and 0.69 µg per mL ATF.

Example 7

Lenses are prepared according to the process detailed in Example 3. Following the dip in the polyacrylic acid solution, the lenses are rinsed in water for 1 minute and then dipped in a 1-propanol solution containing vitamin E oil in concentration ranging from 0.10% (wt/vol) up to 1.5%. Lenses are placed in vials containing phosphate buffered saline and autoclaved for 30 min at 121° C. Measurements of % transmittance showed a decrease in transmittance for those lenses exposed to the higher concentration of vitamin E oil in solution, indicating the upload of vitamin E oil by lenses.

Lenses are prepared according to the process detailed in Example 3. Following the dip in the polyacrylic acid solution, the lenses are placed in 2 mL of phosphate buffered saline containing 0.2% mineral oil (wt/vol) and autoclaved for 30 min at 121° C. Observation of a decrease in surface wettability for lenses packaged in a packaging solution containing mineral oil compared to control samples (i.e., identical lenses packaged in a packaging solution without mineral oil) indicates the upload of mineral oil by lenses.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

The invention claimed is:
1. An ophthalmic product, comprising:
 a sealed package which include a packaging solution and a soft silicone hydrogel contact lens, wherein the soft silicone hydrogel contact lens comprises a polymer matrix and a hydrophobic comfort agent which is not covalently linked to the polymer matrix but distributed therein, wherein the polymeric matrix comprises hydrophobic units derived from a silicone-containing monomer or macromer and hydrophilic units derived from a hydrophilic monomer or macromer,
 wherein the hydrophobic comfort agent is phospholipid, wherein the soft silicone hydrogel contact lens has a capability of gradually releasing the hydrophobic com- fort agent during wear over at least about 4 hours after storing in the packaging solution for at least about one month.

2. The ophthalmic product of claim 1, wherein the soft silicone hydrogel contact lens has at least one property selected from the group consisting of an oxygen permeability of at least about 40 barrers, an elastic modulus of from about 0.2 MPa to about 2.0 MPa, an Ionoflux Diffusion Coefficient D of at least about $1.5 \times 10^{-6}$ mm$^2$/min, a water content of from about 15% to about 70%, a surface hydrophilicity characterized by having an averaged water contact angle of about 90 degrees or less, and combination thereof.

3. The ophthalmic product of claim 2, wherein the soft hydrogel contact lens further comprises a non-crosslinkable hydrophilic polymer as leachable wetting agent, wherein the non-crosslinkable hydrophilic polymer is: a polyvinylalcohol; polyethylene oxide; a polyethylene-polypropylene block copolymer; a polyamide; a polyimide; a polylactone; polyvinylpyrrolidone; a copolymer of N-vinylpyrrolidone and one or more hydrophilic vinylic monomers; a homopolymer of acrylamide or methacrylamide; a copolymer of acrylamide or methacrylamide with one or more hydrophilic vinylic monomers; a homopolymer of N-vinyl formamide, N-vinyl acetamide, N-vinyl isopropylamide, or N-vinyl-N-methyl acetamide; a copolymer of N-vinyl formamide, N-vinyl acetamide, N-vinyl isopropylamide, or N-vinyl-N-methyl acetamide with one or more hydrophilic vinylic monomers, and a mixture thereof.

4. The ophthalmic product of claim 2, wherein the packaging solution comprises from about 0.01% to about 5% by weight of a viscosity-enhancing polymer, wherein the viscosity-enhancing polymer is a water soluble cellulose ether, a water-soluble polyvinylalcohol, a poly(ethylene oxide) having a molecular weight of from about 2000 to about 10,000,000 daltons, a polyvinylpyrrolidone with a molecular weight of from about 30,000 daltons to about 1,000,000 daltons, a copolymer of vinylpyrrolidone with one or more hydrophilic monomers, or a mixture thereof, wherein the water-soluble cellulose ether is methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof.

* * * * *